United States Patent
Chapman et al.

(10) Patent No.: US 9,636,510 B2
(45) Date of Patent: May 2, 2017

(54) DEFIBRILLATOR THAT MONITORS CPR TREATMENT AND ADJUSTS PROTOCOL

(71) Applicant: Physio-Control, Inc., Redmond, WA (US)

(72) Inventors: Fred Chapman, Newcastle, WA (US); Robert G. Walker, Seattle, WA (US); Ronald Eugene Stickney, Edmonds, WA (US)

(73) Assignee: Physio-Control, Inc., Redmond, WA (US)

( * ) Notice: Subject to any disclaimer, the term of this patent is extended or adjusted under 35 U.S.C. 154(b) by 738 days.

(21) Appl. No.: 13/855,487

(22) Filed: Apr. 2, 2013

(65) Prior Publication Data

US 2013/0226255 A1 Aug. 29, 2013

Related U.S. Application Data

(62) Division of application No. 11/095,305, filed on Mar. 31, 2005, now Pat. No. 8,433,407.

(51) Int. Cl.
*A61N 1/39* (2006.01)

(52) U.S. Cl.
CPC ............ *A61N 1/3925* (2013.01); *A61N 1/39* (2013.01); *A61N 1/3993* (2013.01)

(58) Field of Classification Search
CPC ....... A61N 1/3925; A61N 1/39; A61N 1/3993
USPC ......................................................... 607/4–8
See application file for complete search history.

(56) References Cited

U.S. PATENT DOCUMENTS

| | | | |
|---|---|---|---|
| 5,405,362 A * | 4/1995 | Kramer et al. | 607/5 |
| 6,351,671 B1 * | 2/2002 | Myklebust et al. | 607/5 |
| 2004/0143298 A1 * | 7/2004 | Nova et al. | 607/5 |
| 2006/0229680 A1 * | 10/2006 | Chapman et al. | 607/5 |

* cited by examiner

*Primary Examiner* — Tammie K Heller
(74) *Attorney, Agent, or Firm* — Lane Powell PC

(57) ABSTRACT

An apparatus and method is provided for a defibrillator that specifies treatment protocols in terms of number of chest compressions instead of time intervals. The defibrillator includes a connection port that is configured to attach with a plurality of electrodes that are capable of delivery of a defibrillation shock and/or sensing one or more physical parameters. An energy storage device capable of storing a charge is attached to the plurality of electrodes. A controller is coupled to the plurality of electrodes and the energy storage device, the controller is configured to provide CPR chest compression instructions in terms of the numbers of CPR chest compressions.

17 Claims, 2 Drawing Sheets

DEFIBRILLATOR THAT MONITORS CPR TREATMENT AND ADJUSTS PROTOCOL

This application is a division of U.S. application Ser. No. 11/095,305, now issued as U.S. Pat. No. 8,433,407.

TECHNICAL FIELD

The present invention relates generally to defibrillators. More particularly, the present invention relates to defibrillators that monitor CPR treatment and adjust treatment protocols based on the monitored results.

BACKGROUND

A cardiac arrest is a life-threatening medical condition in which a person's heart fails to provide enough blood flow to support life. During a cardiac arrest, the electrical activity may be disorganized (ventricular fibrillation), too rapid (ventricular tachycardia), absent (asystole), or organized at a normal or slow heart rate (pulseless electrical activity). A person treating a cardiac arrest victim may apply a defibrillation pulse to the patient in ventricular fibrillation (VF) or ventricular tachycardia (VT) to stop the unsynchronized or rapid electrical activity and allow a perfusing rhythm to commence. External defibrillation, in particular, is provided by applying a strong electric pulse to the patient's heart through electrodes placed on the surface of the patient's body. The brief pulse of electrical current is provided to halt the fibrillation, giving the heart a chance to start beating with a more normal rhythm. If a patient lacks a detectable pulse but has an ECG rhythm of asystole or pulseless electrical activity (PEA), an appropriate therapy includes cardiopulmonary resuscitation (CPR), which causes some blood flow.

The probability of surviving a cardiac arrest depends on the speed with which appropriate medical care is provided to a patient experiencing the cardiac arrest. To decrease the time until appropriate medical care is provided, it has been recognized that those persons who are first to arrive at the scene, "first responders," should be provided with an automated external defibrillator (AED). An AED that provides adequate instructions to the first responder improves the overall success rate of treating cardiac arrest patients. AEDs are generally designed for use by the first responder, who can be an emergency medical services worker, a firefighter or a police officer, or who can be a layperson with minimal or no AED training. The AED and the first responder work together to deliver resuscitative therapies to the cardiac arrest patient.

Typically, the AED is a small, portable device that analyzes the heart's rhythm and prompts a user to deliver treatment to the patient. Once the AED is activated, it can guide the first responder through each step of the treatment by providing audible and/or visual prompts, that may include CPR treatment and/or a defibrillation pulse, if it determines the desirability for such a pulse. Protocols have been developed for AEDs that typically provide instructions in time intervals, based on medical standards. These protocols generally call for CPR to be administered by the first responder in time intervals of a pre-programmed length, such as "do one minute of CPR".

Unfortunately, under the pressures of an emergency situation, it can difficult for a first responder to accurately judge time intervals designated by the AED for CPR treatment. In addition, different first responders may differ in technique and may not consistently provide adequate CPR treatment during the time period designated by the AED.

Accordingly, it is desirable to provide a method and apparatus that quickly, accurately, and automatically prompts a first responder to provide CPR treatment or defibrillation, as appropriate, in an emergency situation. Furthermore, other desirable features and characteristics of the present invention will become apparent from the subsequent detailed description and the appended claims, taken in conjunction with the accompanying drawings and the foregoing technical field and background.

BRIEF SUMMARY

A defibrillator is disclosed that specifies treatment protocols in terms of number of chest compressions instead of time intervals. The defibrillator includes a connection port that is configured to attach with a plurality of electrodes that are capable of delivery of a defibrillation shock and/or sensing one or more physical parameters. An energy storage device capable of storing a charge is attached to the plurality of electrodes. A controller is coupled to the plurality of electrodes and the energy storage device, the controller is configured to provide CPR chest compression instructions in terms of the numbers of CPR chest compressions. The defibrillator may also monitor the patient during periods of CPR and count chest compressions as they are administered and then use the information it gathers on compressions to gate and/or adjust its protocol.

A defibrillator is disclosed that includes a means for selecting a CPR treatment protocol from a plurality of stored CPR treatment protocols. The selected CPR treatment protocol includes at least the number of CPR chest compressions. And a means for communicating the number of CPR chest compressions.

A method is disclosed of operating a defibrillator in conjunction with the delivery of an injected medication. The method includes selecting a CPR treatment protocol from a plurality of CPR treatment protocols corresponding to the injected medication. The CPR treatment protocol includes at least chest compression and defibrillator pulse instructions. Communicating at least the number of chest compressions of the CPR treatment protocol.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

Figure 1:
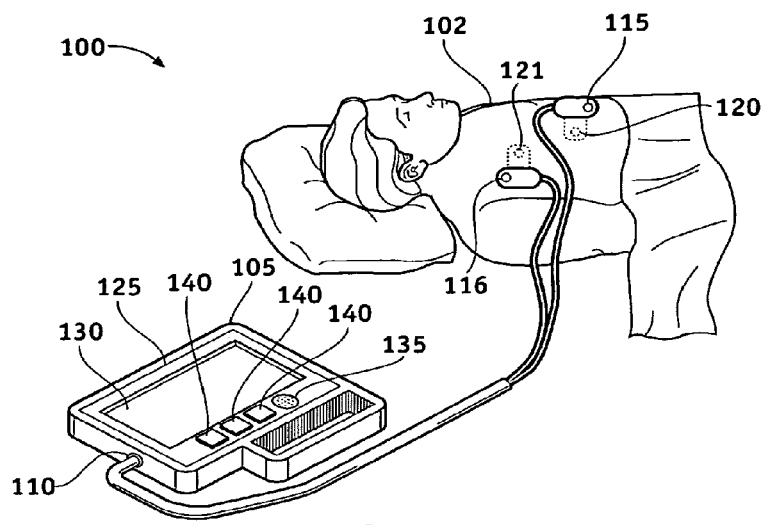
FIG. 1 is a simplified schematic view of an AED connected to a patient in accordance with an exemplary embodiment of the invention.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of defibrillator implementations and that the system described herein is merely one exemplary application for the invention.

For the sake of brevity, conventional techniques related to defibrillator devices, related control signal processing, data transmission, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

It is sometimes difficult for a user, or "first responder", and an external defibrillating system to work effectively together to efficiently deliver resuscitative therapies. Current protocols have been developed that specify time intervals for the application of CPR. While the external defibrillating system is good at measuring time intervals, a stressed first responder may be poor at judging the length of time intervals and cannot reliably anticipate when that time interval will conclude. Furthermore, with different first responders having different training and techniques, specifying a time interval may result in drastically different CPR therapies, since the benefit does not come solely from the time interval but comes from actively compressing the chest enough times during that interval.

The invention described herein is a method and apparatus that includes an algorithm that makes it possible to specify treatment protocols in terms of number of chest compressions instead of time intervals. The external defibrillating system disclosed may also monitor the patient during periods of CPR treatment and count chest compressions as they are administered and then use the information it gathers on chest compressions to gate and/or adjust the treatment protocol.

The invention is directed to an external defibrillating system that may be an Automated or Automatic External Defibrillator (AED) or a manual monitor/defibrillator. While many of the exemplary embodiments of the invention apply to all types of external defibrillators, some of the embodiments are only for specific types, such as embodiments only for automated defibrillators or only for manual monitor/defibrillators FIG. 1 shows one embodiment of an external defibrillating system 100 configured to be able to deliver a CPR treatment protocol, including a defibrillation pulse if needed, to a patient. The system 100, includes, but is not limited to, a defibrillator 105 having a connection port 110 that is configured to electrically connect the defibrillator 105 to one or more electrodes 115,116. The defibrillator 105 can be any number of external defibrillators in accordance with the present invention.

The defibrillator 105 preferably includes a user interface 125 having a display 130 configured to visually present to the user various measured or calculated parameters associated with the patient 102 and/or other information to a user of the defibrillator 105. For example, the display 130 can be configured to visually present the ECG and/or other physiological signals indicating the physical status of the patient 102, or instructions and/or commands, including prompts to perform cardiopulmonary resuscitation (CPR) treatment or other treatment instructions, to the user. The display 130 can also be configured to present visual alerts, flashing lights or warnings to the user. The user interface 125 also includes an audio system 135 that provides an audio signal to aurally communicate with the user voice prompts that deliver instructions or commands, monotonal, ascending, descending or quickening tones to indicate alerts or warnings, or any other suitable audio signals for communicating with the user. The user interface 125 can also include one or more input devices (e.g., switches or buttons) 140 that are configured to receive commands or information from the operator, such as, in the case of automated or manual defibrillators, a shock command. Additionally, the visual display 130 and audio system 135 may be configured to cooperate with one another The defibrillator 105 is configured to generate a charge that is delivered to the patient 102 as a defibrillation pulse with one or more electrodes 115, 116. The one or more electrodes 115, 116 may also be configured to sense one or more physiological and/or physical parameters of the patient 102 and supply signals representative of these parameters to the defibrillator 105. The one or more physiological and/or physical parameters of the patient can include information about the patient's heart, blood, temperature and/or the like. More particularly, the sensed physical parameter can also be ECG data, heart rhythm data, heart rate data, cardiac output data, blood flow data, a patient's level of perfusion, respiration data and/or any other physical parameter that is used in the art to assess the physical condition of a patient. As shown in phantom in FIG. 1, the defibrillator 105 may additionally include one or more sensing electrodes 120, 121 to sense the physiological and/or physical parameters. In either configuration, the signals provided by the one or more electrodes 115, 116 and/or one or more sensing electrodes 120, 121 are preferably evaluated by the defibrillator 105 to evaluate and determine, among other things, selection of an appropriate CPR treatment protocol from a plurality of CPR protocols stored in the defibrillator 105. It can also determine whether a defibrillation pulse should be applied to patient 102 in accordance with techniques known to those of ordinary skill in the art. The defibrillator 105 can also evaluate the signals provided by the one or more electrodes 115,116 and/or one or more sensing electrodes 120, 121 to determine the waveform parameters (e.g., voltage, current, energy and/or duration), as well as magnitude and duration of the defibrillation pulse.

Counting chest compressions may be accomplished by a number of different physiological or physical signals. One or more of the physiological or physical signals could also provide a count of breaths (ventilation), which would augment the information provided by the compression counter. In one embodiment, chest compressions could be based on the continuous high frequency impedance signal which fluctuates substantially when the chest is compressed. The continuous high frequency impedance signal may be present in the external defibrillating system. In another embodiment, the compression count could be based on an electrocardiogram (ECG) signal, which generally exhibits substantial "artifact" during compression. In still another embodiment, the compression count could be based on an accelerometer or pressure sensor attached to the chest, optionally as part of the defibrillation electrode. In yet another embodiment, the compression count could be based on physiological signals, such as a plethysmographic waveform used by pulse oximeters.

Figure 2:
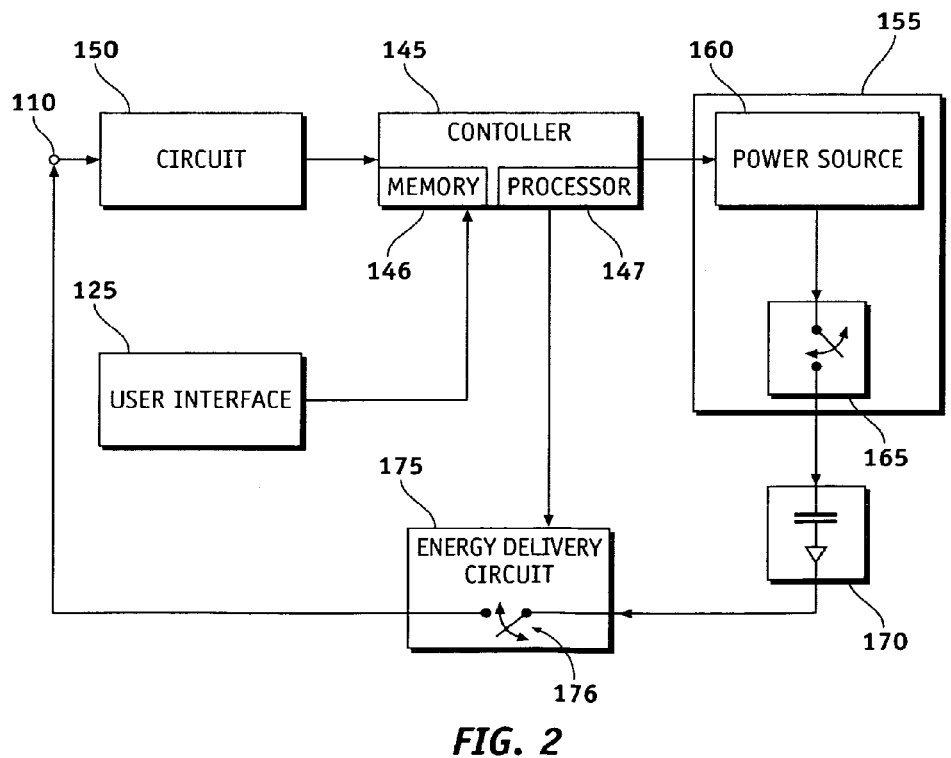
FIG. 2 is a simplified block diagram of an AED in accordance with one embodiment of the invention.

FIG. 2 shows one embodiment of a simplified block diagram of the circuitry that makes up the defibrillator 105. The defibrillator 105 preferably includes a controller 145, the user interface 125 (e.g., switches or buttons 140 and/or display 130 as shown in FIG. 1), a circuit 150, a charging mechanism 155 that can include a power source 160 and a switch 165 to couple the power source 160 to the one or more energy storage devices (e.g., capacitors) 170 and an energy delivery circuit 175, which is illustrated as a switch 176 that is configured to selectively couple the one or more energy storage devices 170 to the connection port 110 under the control of the controller 145. The energy delivery circuit 175 can be implemented with any number of circuit configurations. The controller 145 can be a single processing unit or multiple processing units and can be implemented with software, hardware, firmware, or any combination thereof. The controller 145 is configured to at least partially control the operation of the defibrillator 105. This may include the plurality of treatment protocols and charging the one or more energy storage devices 170. It will be appreciated that the circuitry depicted in FIG. 2 is merely exemplary of a particular architecture, and that numerous other circuit architectures may be used to implement the operation of the defibrillator 105.

The controller 145 may include, among other things, a processor 147 and a memory unit 146. The processor 147 may be any one of numerous known general purpose processors or an application specific processor that operates in response to program instructions, which may be stored in any of various forms of memory storage. It will also be appreciated that the controller 145 may be implemented using various other circuits, not just a programmable processor. The memory unit 146 is in operable communication with processing unit 147.

The memory unit 146 may contain the operating system, software routines and a plurality of CPR treatment protocols. The CPR treatment protocols may include at least chest compression and defibrillator pulse treatment instructions. The CPR treatment protocols may also include predetermined parameters based on the sensed physical parameters such things as the administration of oxygen therapy, drug therapy, or, checking the patient for a pulse or for normal breathing, monitoring $SaO_2$, monitoring end tidal $CO_2$, or blood pressure levels, or any other non-electric treatment known in the art that is appropriately administered to a patient with an arrhythmic heart condition. The memory 146 can also receive and store the patient's sensed physical parameters, historical data, lengths of time and rate of CPR treatments and defibrillation pulses previously discharged to the patient.

It will be appreciated that the above-mentioned scheme is merely exemplary of one scheme for storing operating software and software routines, and that various other storage schemes may be implemented. It will be appreciated that the memory unit 146 could be integrally formed as part of the controller 145 and/or processing unit 147, or could be part of a device or system that is physically separate from the defibrillator 105.

In use, the defibrillator 105 makes treatment determinations based on the sensed physical parameters by comparing the sensed physical parameters to predetermined CPR treatment protocols stored in the memory unit 146. The defibrillator 105 determines which of the stored CPR treatment protocols should be used to deliver the appropriate chest compressions and/or rate based on the sensed physical parameters and whether a patient should receive a defibrillation pulse, such as a shock. The appropriate CPR treatment protocol is then communicated to the user. The controller 145 is configured to automatically update and/or continuously sense the sensed physical parameters and adjust the CPR treatment protocol accordingly.

The CPR treatment protocols described herein are specified in terms of numbers of chest compressions and communicated to the user in that fashion. With this approach, the defibrillator 105 instructs the user to deliver a certain number of chest compressions, rather than provide CPR for a certain time interval. There are many different ways that the desired number of chest compressions may be conveyed to the user. For example, the defibrillator 105 may count the number of chest compressions with the user. This may be used to pace the chest compression rate. The defibrillator 105 may communicate total chest compression count, such as "apply 100 chest compressions". The defibrillator may communicate updated compression information, such as "20 more compressions starting now". The defibrillator may communicate a "pre-shock" sprint before a defibrillation pulse is applied, such as "do 50 compressions and then press the defibrillate button".

Figure 3:
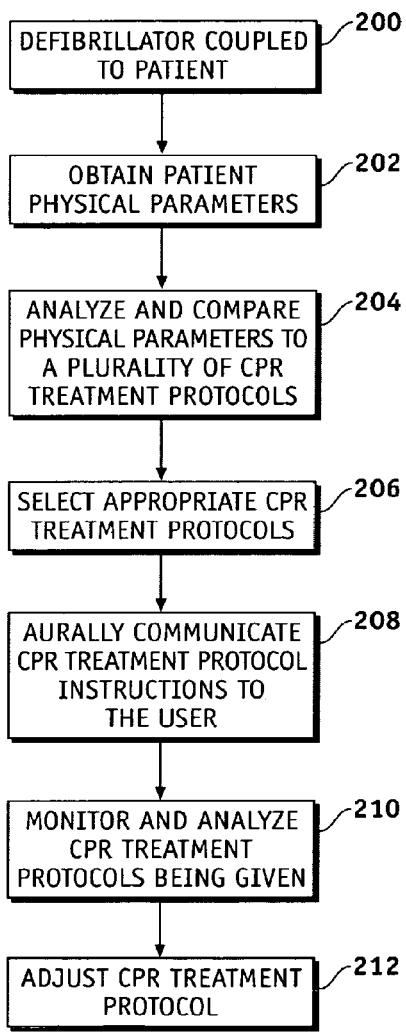
FIG. 3 is a flowchart for the method of operating the AED of FIG. 1 in accordance with one embodiment of the present invention.

FIG. 3 shows one method of operating a defibrillator according to the present invention, such as defibrillator 105 shown in FIG. 1. The defibrillator is coupled to a patient at step 200. At step 202, one or more physical parameters of the patient are obtained from the patient via the one or more electrodes 115, 116, 120, 121. It will be appreciated that any number of physical parameters can be sensed. Once the defibrillator 105 receives the signals at step 204, the one or more physical parameters are analyzed and compared to a plurality of CPR treatment protocols stored in the memory unit 146 of the controller 145 to determine whether or not the patient's physical parameters indicate a condition that should be treated with chest compressions or a defibrillation pulse. The controller 145 then selects the appropriate CPR treatment protocol based in the one or more physical parameters at step 206. The appropriate CPR treatment protocol is then aurally communicated to the user at step 208. The aurally communicated information includes at least chest compression and defibrillator pulse treatment instructions. The appropriate CPR treatment protocol may also be displayed on the display 130.

The controller 145 is configured to automatically update and/or continuously sense the sensed physical parameters at step 210 to determine the number of chest compressions and/breaths being given the patient. For example, in one embodiment of the invention, counting the number chest compressions may be based on an electrocardiogram (ECG) signal. In other embodiments, counting the number chest compressions may be based on high frequency impedance, an acceleration sensor signal, a pressure sensor signal, or an impedance plethysmographic waveform. The controller 145 then adjusts the CPR treatment protocol accordingly based on the monitored information at step 212.

Figure 4:
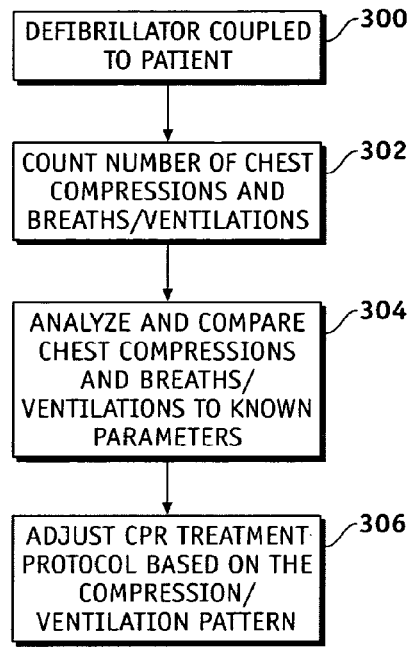
FIG. 4 is a flowchart for the method of determining the number of users of the AED of FIG. 1 in accordance with one embodiment of the present invention.

FIG. 4 shows one method in which an AED may be able to determine a user's technique by monitoring the pattern of chest compressions and/or breaths given to the patient. The AED may then adjust the CPR treatment accordingly. Rescuers are often trained to deliver either fifteen compressions followed by two breaths (recommended for CPR with an unsecured airway) or continuous chest compressions with asynchronous ventilation (recommended for CPR with an intubated airway). Based on this information, the defibrillator 105 can optimize the CPR treatment protocol based on the knowledge that the CPR was being administered in a pattern taught for an unsecured or secured airway. In use, the AED is coupled to the patient at step 300. The number of chest compressions and/or breaths/ventilations is obtained from the patient via the one or more electrodes at step 302 by known means, such as high frequency impedance. Once the AED receives the signals at step 304, the numbers of chest compressions and/or breaths/ventilations are analyzed and compared to a plurality of CPR treatment techniques stored in the memory unit of the AED to determine compression/ventilation pattern. The AED then adjusts the appropriate CPR treatment protocol based on the compression/ventilation pattern at step 306.

By monitoring the chest compression count given to the patient, the AED can make immediate changes to the CPR treatment protocol. In one embodiment, the AED could use compression count to determine compression rate and provide feedback to the user to speed up or slow down. In another embodiment, the AED is able to detect the slowdown of compressions, which may indicate onset of fatigue by the user and prematurely call the end of the CPR interval in favor of delivering a defibrillation pulse. In another embodiment, the AED could detect if the rate of chest compressions is low or non-existent. For example, if no compressions are detected during CPR treatment, prompts to "start CPR" may be given. Also, if compressions are detected but the rate is so slow to be ineffective, the AED could cut short the CPR treatment segment and defibrillate.

In another embodiment, the AED may be able to determine if the user is doing compression-only CPR by monitoring the chest compression count and ventilations given to the patient. Some of the CPR treatment protocols may vary treatments for chest compressions and ventilations. While chest compressions without ventilations may be appropriate for the first few minutes of resuscitation effort, ventilations are best added later in the resuscitation after oxygen has been depleted from the circulating blood. For example, if the AED sensed administration of compression-only CPR, it could advise after a pre-set amount of time or number of chest compressions that ventilations be added to the CPR compressions.

Figure 5:
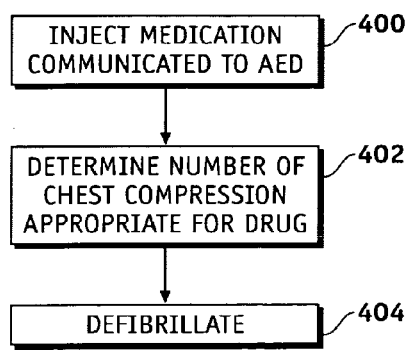
FIG. 5 is a flowchart for the method of operating the AED of FIG. 1 in conjunction with a drug injection in accordance with one embodiment of the present invention.

FIG. 5 shows one method in which a defibrillator is used with medication injection to assure adequate circulation of injected drugs, such as epinephrine, before delivery of a defibrillation pulse. The coronary perfusion pressure elevating effects of epinephrine during CPR is rather short-lived and there is a "sweet spot" amount of chest compressions that should be delivered between injection of the epinephrine and defibrillation. Often, defibrillation pulse treatments are administered too early or too late. Too early and the heart has not received the boost in circulation; too late and the effects of circulation have worn off. So the CPR treatment protocol selected could optimize the effectiveness of an injection by instructing and counting compressions after injection, and then shocking after an appropriate amount of circulation. The injected drug is communicated to the defibrillator at step 400. At step 402 the defibrillator counts the chest compressions for the treatment and prompts for delivery of a defibrillation pulse 404. In terms of compressions after injection of epinephrine, this may be in the neighborhood of 200 compressions.

The AED compression count may also be combined with "viability index" information provided by a ventricular fibrillation (VF) analysis algorithm. If the chest compression rate is good and yet the viability index continues to worsen, it would be clear that CPR treatment is not effective. This could indicate the need to improve the CPR chest compressions, such as instruction the user to "Press harder on the chest", or alter the CPR treatment protocol, for example to administer a peripheral vasoconstrictor drug, such as epinephrine.

While the defibrillator described herein instructs the user with CPR treatment protocols based on chest compression count, it is envisioned that an defibrillator could be designed to also instruct the user with time intervals in addition chest compression count. In this way, a single device could be sold to users wanting to continue using time intervals as well as users wanting chest compression counts.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A defibrillator, comprising:
   means for selecting a CPR treatment protocol from a plurality of stored CPR treatment protocols, the selected CPR treatment protocol including at least a number of CPR chest compressions;
   means for communicating the number of CPR chest compressions; and
   means for performing an ECG analysis, and wherein the selected CPR treatment protocol includes an initial number of chest compressions prior to an initial ECG analysis.

2. The defibrillator of claim 1, further comprising means for counting the number of chest compressions as they are administered.

3. The defibrillator of claim 1, wherein the selected CPR treatment protocol further includes a number of chest compressions between an ECG analysis and a defibrillation pulse.

4. The defibrillator of claim 1, further comprising:
   means for monitoring CPR treatment; and
   means for adjusting CPR chest compressions by selecting a new CPR treatment protocol from the plurality of stored CPR treatment protocols based at least in part on the monitored CPR treatment, the new CPR treatment protocol including at least a number of CPR chest compressions.

5. A method of operating a defibrillator in conjunction with a delivery of an injected medication, the method comprising:
   selecting a CPR treatment protocol from a plurality of CPR treatment protocols corresponding to the injected medication, the selected CPR treatment protocol including at least chest compression and defibrillator pulse instructions; and aurally communicating at least a number of chest compressions of the selected CPR treatment protocol.

6. The method of claim 5, further comprising:

counting the number of chest compressions as they are administered from the injection of the medication to a predetermined condition for delivery of a defibrillator pulse; and delivering a defibrillator pulse at the predetermined condition.

7. The method of claim 6, further comprising:

monitoring CPR treatment;

adjusting CPR chest compressions by selecting a new CPR treatment protocol based at least in part on the monitored CPR treatment, the new CPR treatment protocol including at least chest compression; and communicating at least the number of chest compression of the new CPR treatment protocol.

8. The method of claim 6, wherein the predetermined condition is an optimal condition.

9. A defibrillator, comprising:

a controller configured to select a CPR treatment protocol from a plurality of stored CPR treatment protocols and to perform an ECG analysis from data received via a sensing electrode, the selected CPR treatment protocol including an initial number of chest compressions prior to an initial ECG analysis; and an output device for communicating the number of CPR chest compressions.

10. The defibrillator of claim 9 in which the controller is further configured to count the number of chest compressions as they are administered.

11. The defibrillator of claim 10, wherein the selected CPR treatment protocol further includes a number of chest compressions between an ECG analysis and a defibrillation pulse.

12. The defibrillator of claim 10, wherein the controller counts the number of chest compressions based on an ECG signal, high frequency impedance, an acceleration sensor signal, a pressure sensor signal, or an impedance plethysmographic waveform.

13. The defibrillator of claim 9, further comprising:

sensors configured to monitor CPR treatment, wherein the controller is further configured to adjust CPR chest compressions by selecting a new CPR treatment protocol from the plurality of stored CPR treatment protocols based at least in part on the monitored CPR treatment, the new CPR treatment protocol including at least a number of CPR chest compressions.

14. A method of operating a defibrillator, the method comprising:

selecting a CPR treatment protocol from a plurality of stored CPR treatment protocols, the selected CPR treatment protocol including at least a number of CPR chest compressions;

communicating the number of CPR chest compressions; and performing an ECG analysis, wherein the selected CPR treatment protocol includes an initial number of chest compressions prior to an initial ECG analysis.

15. The method of claim 14, further comprising counting the number of chest compressions as they are administered.

16. The method of claim 14, wherein the selected CPR treatment protocol further includes a number of chest compressions between an ECG analysis and a defibrillation pulse.

17. The method of claim 14, further comprising:

monitoring CPR treatment; and adjusting CPR chest compressions by selecting a new CPR treatment protocol from the plurality of stored CPR treatment protocols based at least in part on the monitored CPR treatment, the new CPR treatment protocol including at least a number of CPR chest compressions.

* * * * *